US009897622B2

(12) United States Patent
Horiuchi et al.

(10) Patent No.: US 9,897,622 B2
(45) Date of Patent: Feb. 20, 2018

(54) AUTOMATIC ANALYZER

(71) Applicant: HITACHI HIGH-TECHNOLOGIES CORPORATION, Tokyo (JP)

(72) Inventors: Rie Horiuchi, Tokyo (JP); Yoshihiro Suzuki, Tokyo (JP); Takashi Nakasawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 127 days.

(21) Appl. No.: 14/784,424

(22) PCT Filed: Apr. 1, 2014

(86) PCT No.: PCT/JP2014/059688
§ 371 (c)(1),
(2) Date: Oct. 14, 2015

(87) PCT Pub. No.: WO2014/175018
PCT Pub. Date: Oct. 30, 2014

(65) Prior Publication Data
US 2016/0069922 A1  Mar. 10, 2016

(30) Foreign Application Priority Data
Apr. 22, 2013 (JP) .................................. 2013-089343

(51) Int. Cl.
*G01N 21/01* (2006.01)
*G01N 35/10* (2006.01)
(Continued)

(52) U.S. Cl.
CPC ........... *G01N 35/1004* (2013.01); *B08B 3/08* (2013.01); *G01N 21/15* (2013.01); *G01N 21/75* (2013.01)

(58) Field of Classification Search
CPC .................. G01N 35/1004; G01N 35/1006
(Continued)

(56) References Cited

U.S. PATENT DOCUMENTS 4,299,244 A * 11/1981 Hirai ...................... A61B 1/123
134/102.1
4,307,741 A * 12/1981 Rossi ....................... B08B 3/02
134/100.1

(Continued)

FOREIGN PATENT DOCUMENTS

JP      5-38833 Y2     9/1993
JP    2005-181338 A    7/2005
(Continued)

OTHER PUBLICATIONS

International Search Report and Written Opinion of PCT/JP2014/059688.
(Continued)

Primary Examiner — Jason McCormack
(74) Attorney, Agent, or Firm — Mattingly & Malur, PC

(57) ABSTRACT

A detergent reservoir reserves detergent for cleaning of a sample probe and includes a cleaning liquid supply port, a detergent supply port, and a waste liquid port When a predetermined condition for execution of cleaning of the detergent reservoir is not satisfied, and a remaining amount of the detergent reserved in the detergent reservoir is a predetermined amount or less, a pump is operated to increase the remaining amount of the detergent to the predetermined amount; and when the predetermined condition for execution of cleaning of the detergent reservoir is satisfied, a solenoid valve is opened to dispose of the detergent in the detergent reservoir. Then, after the detergent
(Continued)

in the detergent reservoir is disposed of, the solenoid valve is closed, and a pump is operated to supply cleaning liquid to the detergent reservoir.

19 Claims, 10 Drawing Sheets

(51) Int. Cl.
  *B08B 3/08* (2006.01)
  *G01N 21/15* (2006.01)
  *G01N 21/75* (2006.01)
(58) Field of Classification Search
  USPC .................................................. 250/431, 428
  See application file for complete search history.

(56) References Cited

U.S. PATENT DOCUMENTS

| | | |
|---|---|---|
| 2005/0153426 A1 | 7/2005 | Muller et al. |
| 2011/0017238 A1 | 1/2011 | Kuroda |
| 2011/0174343 A1* | 7/2011 | Azuma ............... G01N 35/1016 134/113 |
| 2011/0293474 A1* | 12/2011 | Sugimura .......... G01N 35/1004 422/62 |
| 2012/0318302 A1* | 12/2012 | Nakayama ......... G01N 35/1004 134/26 |

FOREIGN PATENT DOCUMENTS

| | | |
|---|---|---|
| JP | 2007-047038 A | 2/2007 |
| JP | 2008-202945 A | 9/2008 |
| JP | 2008-224245 A | 9/2008 |
| JP | 2009-222593 A | 10/2009 |
| JP | 2010-071897 A | 4/2010 |
| JP | 2011-257248 A | 12/2011 |
| JP | 2012-8123 A | 1/2012 |
| WO | 2008/108328 A1 | 9/2008 |

OTHER PUBLICATIONS

International Preliminary Report on Patentability received in corresponding International Application No. PCT/JP2014/059688 dated Nov. 12, 2015.

* cited by examiner

AUTOMATIC ANALYZER

TECHNICAL FIELD

The present invention relates to an automatic analyzer for conducting qualitative/quantitative analyses of a sample such as blood and urine, and more specifically relates to an automatic analyzer including a detergent reservoir for use in cleaning of a dispensation probe.

BACKGROUND ART

An automatic analyzer for a clinical test is an apparatus for measuring specific components in a biological sample such as blood and urine. A general operation thereof is as follows. The automatic analyzer dispenses a sample and a reagent into a reaction cuvette with use of dedicated dispensation probes, stirs the sample and the reagent to cause a reaction, and performs concentration calculation for a target item based on information such as the absorbance and the emitting amount of light obtained from a reaction liquid.

An inner wall and an outer wall of the dispensation probe are cleaned with purified water before dispensing the following sample. However, in rare cases, the dispensation probe cannot completely be cleaned with purified water due to the liquid property or the contained components (protein, fat, and the like) of the sample, and the previous sample may influence a measurement result of the following sample.

As a preventive measure thereof, the dispensation probe is additionally cleaned with detergent. A general operation thereof is as follows. The automatic analyzer sucks detergent from an external detergent bottle with use of the dispensation probe, discharges the detergent in a cleaning bath, and cleans the inner wall and the outer wall of the dispensation probe with purified water.

However, the dispensation probe cannot be cleaned when the amount of the detergent decreases. In this case, the automatic analyzer needs to be set in a standby (measurement stopping) state to refill the detergent. This causes a problem in which the detergent refilling work is troublesome and a problem in which the analysis processing amount per unit time decreases as much as the period in which the measurement is interrupted.

To solve the above problems, an automatic analyzer including a detergent reservoir in which detergent refilling is automated is known (e.g., see PTL 1 to 3).

CITATION LIST

Patent Literature

PTL 1: Publication of JP 2008-202945 A
PTL 2: Publication of JP 2010-71897 A
PTL 3: Publication of JP 2011-257248 A

SUMMARY OF INVENTION

Technical Problem

In general, the detergent to be used for cleaning the dispensation probe is alkaline detergent. When the detergent is left for a long time, water in the detergent evaporates. Consequently, a crystal is deposited on an inner wall of the detergent reservoir.

Here, in the detergent reservoir disclosed in each of PTL 1 to 3, the crystal may flow due to the detergent automatically refilled and float in the detergent. When the crystal is sucked by the dispensation nozzle at the time of cleaning of the dispensation nozzle, this may cause clogging of the dispensation nozzle and bring about measurement data failure.

To avoid the above risks (the clogging of the dispensation nozzle, the measurement data failure, and the like), the crystal deposited in the detergent reservoir must be removed periodically. In the conventional automatic analyzer, this removing work needs to be performed manually by an operator after the analyzer is set in the standby state. This causes a problem in which the detergent reservoir cleaning work is troublesome and a problem in which the analysis processing amount per unit time decreases as much as the period in which the measurement is interrupted.

An object of the invention is to provide an automatic analyzer capable of reducing trouble of detergent reservoir cleaning work and restricting a decrease in the analysis processing amount due to the detergent reservoir cleaning.

Solution to Problem

To achieve the above object, an automatic analyzer according to the present invention includes a cleaning bath in which cleaning of the probe is performed with purified water, a sample dispensation mechanism dispensing a sample with use of a probe, a detergent reservoir including at least one cleaning liquid supply port, a detergent supply port, and a waste liquid port and reserving detergent for cleaning of the probe and in which, in a case in which the probe needs to be additionally cleaned based on a liquid property or a contained component of the sample, the probe is cleaned with the detergent a cleaning liquid tank which stores a cleaning liquid, a detergent tank which stores the detergent for cleaning of the detergent reservoir, a waste liquid tank which stores a waste liquid, a first pump installed on a flow path connecting the cleaning liquid tank with the cleaning liquid supply port; a second pump installed on a flow path connecting the detergent tank with the detergent supply port; a solenoid valve installed on a flow path connecting the waste liquid port with the waste liquid tank; and a control unit executing first control in which, in a case in which a predetermined condition for execution of cleaning of the detergent reservoir is not satisfied, and in which a remaining amount of the detergent reserved in the detergent reservoir is a predetermined amount or less, the second pump is operated to increase the remaining amount of the detergent to the predetermined amount, and second control in which, in a case in which the predetermined condition for execution of cleaning of the detergent reservoir is satisfied, the solenoid valve is opened to dispose of the detergent in the detergent reservoir, after the detergent in the detergent reservoir is disposed of, the solenoid valve is closed, and the first pump is operated to supply the cleaning liquid to the detergent reservoir.

Advantageous Effects of Invention

According to the present invention, it is possible to reduce trouble of detergent reservoir cleaning work and restrict a decrease in the analysis processing amount due to the detergent reservoir cleaning. Problems, configurations, and effects other than the above will be made clear by the following description of embodiments.

DESCRIPTION OF EMBODIMENTS (First Embodiment)

Hereinbelow, a configuration and an operation of an automatic analyzer 1000 as a first embodiment of the present invention will be described with reference to FIGS. 1 to 5. It is to be noted that a rack-type automatic analyzer for a clinical test conducting an analysis of a biological sample such as blood and urine will be described as an example, and that the present invention is not limited to this.

Figure 1:
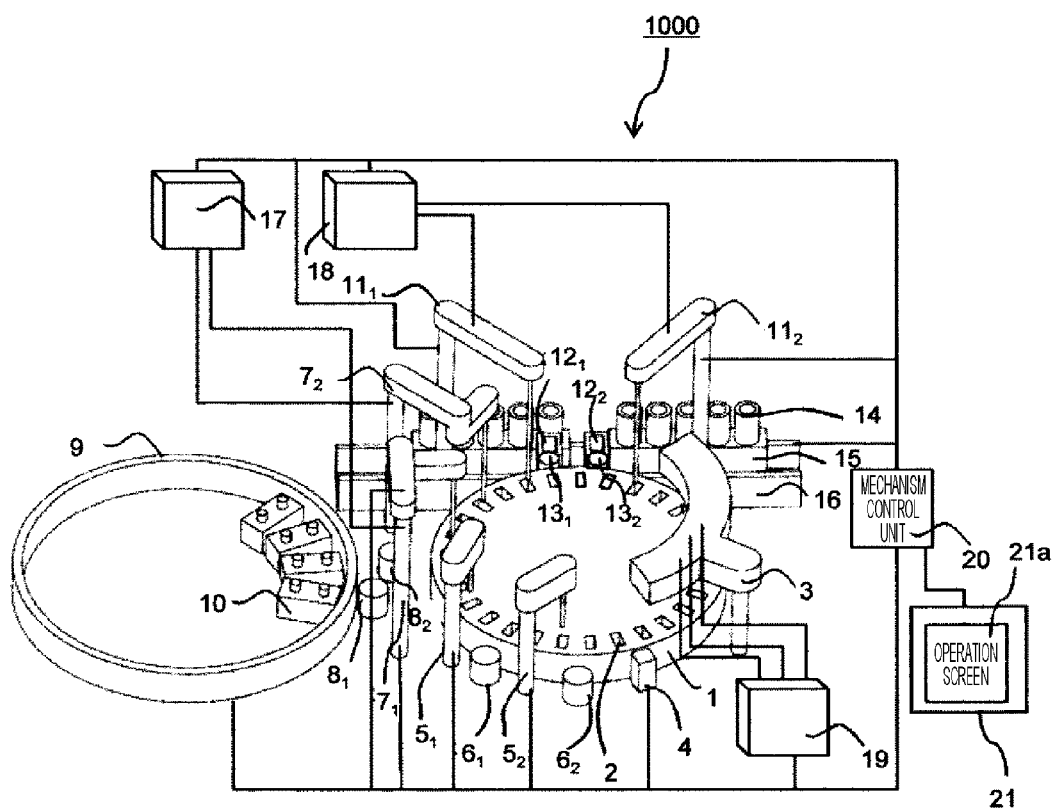
FIG. 1 is a configuration diagram of an automatic analyzer as a first embodiment of the present invention.

First, an entire configuration of the automatic analyzer 1000 as the first embodiment of the present invention will be described with reference to FIG. 1. FIG. 1 is a configuration diagram of the automatic analyzer 1000 as the first embodiment of the present invention.

The automatic analyzer 1000 includes a reaction disk 1, a reaction cuvette 2, a washing mechanism 3 for the reaction cuvette 2, a photometer 4, a stirring mechanism 5 ($5_1$ to $5_2$), a cleaning bath 6 ($6_1$ to $6_2$) for cleaning a stirrer of the stirring mechanism 5, a reagent dispensation mechanism 7 ($7_1$ to $7_2$), a cleaning bath 8 ($8_1$ to $8_2$) for cleaning a dispensation probe of the reagent dispensation mechanism 7, a reagent disk 9, a reagent bottle 10 containing each of various reagents, a sample dispensation mechanism 11 ($11_1$ to $11_2$), a cleaning bath 12 ($12_1$ to $12_2$) for cleaning a dispensation probe of the sample dispensation mechanism 11, a detergent reservoir unit 13 ($13_1$ to $13_2$) for reserving detergent for the sample dispensation mechanism 11, a sample container 14, a rack 15 for transporting the sample container 14, and a sample transport mechanism 16.

The reaction cuvettes 2 are arranged concentrically on the reaction disk 1. The reagent bottles 10 are arranged concentrically on the reagent disk 9. To the reagent dispensation mechanism 7, a reagent pump 17 is connected. To the sample dispensation mechanism 11, a sample pump 18 is connected. To the washing mechanism 3, a washing pump 19 is connected.

A mechanism control unit 20 includes a processor, a memory, and the like and controls operations of the respective mechanisms. Also, an operator can instruct the mechanism control unit 20 to perform operations via an operation screen 21a displayed on a display unit 21. The operation instructions are input with use of input devices such as a keyboard, a mouse, and a touch panel.

An analysis is conducted by the automatic analyzer in the following procedure. First, the sample dispensation mechanism 11 ($11_1$ to $11_2$) dispenses a sample to be analyzed from the sample container 14 to the reaction cuvette 2. Subsequently, the reagent dispensation mechanism 7 ($7_1$ to $7_2$) dispenses a reagent to be used in the analysis from the reagent bottle 10 to the reaction cuvette 2. Subsequently, the stirring mechanism 5 ($5_1$ to $5_2$) stirs a reaction liquid.

The photometer 4 performs photometric measurement of the reaction liquid each time the reaction cuvette 2 passes in front of the photometer 4. The mechanism control unit performs concentration calculation for an analysis target item based on photometric data. The display unit 21 (information equipment) displays a result obtained by the concentration calculation.

The stirrer of the stirring mechanism 5 ($5_1$ to $5_2$) is cleaned in the cleaning bath 6 ($6_1$ to $6_2$) each time of stirring. The dispensation probe of the reagent dispensation mechanism 7 ($7_1$ to $7_2$) is cleaned in the cleaning bath 8 ($8_1$ to $8_2$) each time of dispensation. The dispensation probe of the sample dispensation mechanism 11 ($11_1$ to $11_2$) is cleaned in the cleaning bath 12 ($12_1$ to $12_2$) each time of dispensation. In the cleaning baths 6, 8, and 12, cleaning is performed with purified water.

In the present embodiment, in a case in which the sample dispensation probe needs to be additionally cleaned based on the liquid property or the contained components of the sample, the sample dispensation probe is cleaned with detergent in the detergent reservoir unit 13 ($13_1$ to $13_2$).

Also, the reaction cuvette 2 after the photometric measurement is cleaned by the washing mechanism 3 and is repetitively used for the following analyses. A detergent reservoir system including the detergent reservoir unit 13 will be described in detail below with reference to FIG. 2.

Figure 2:
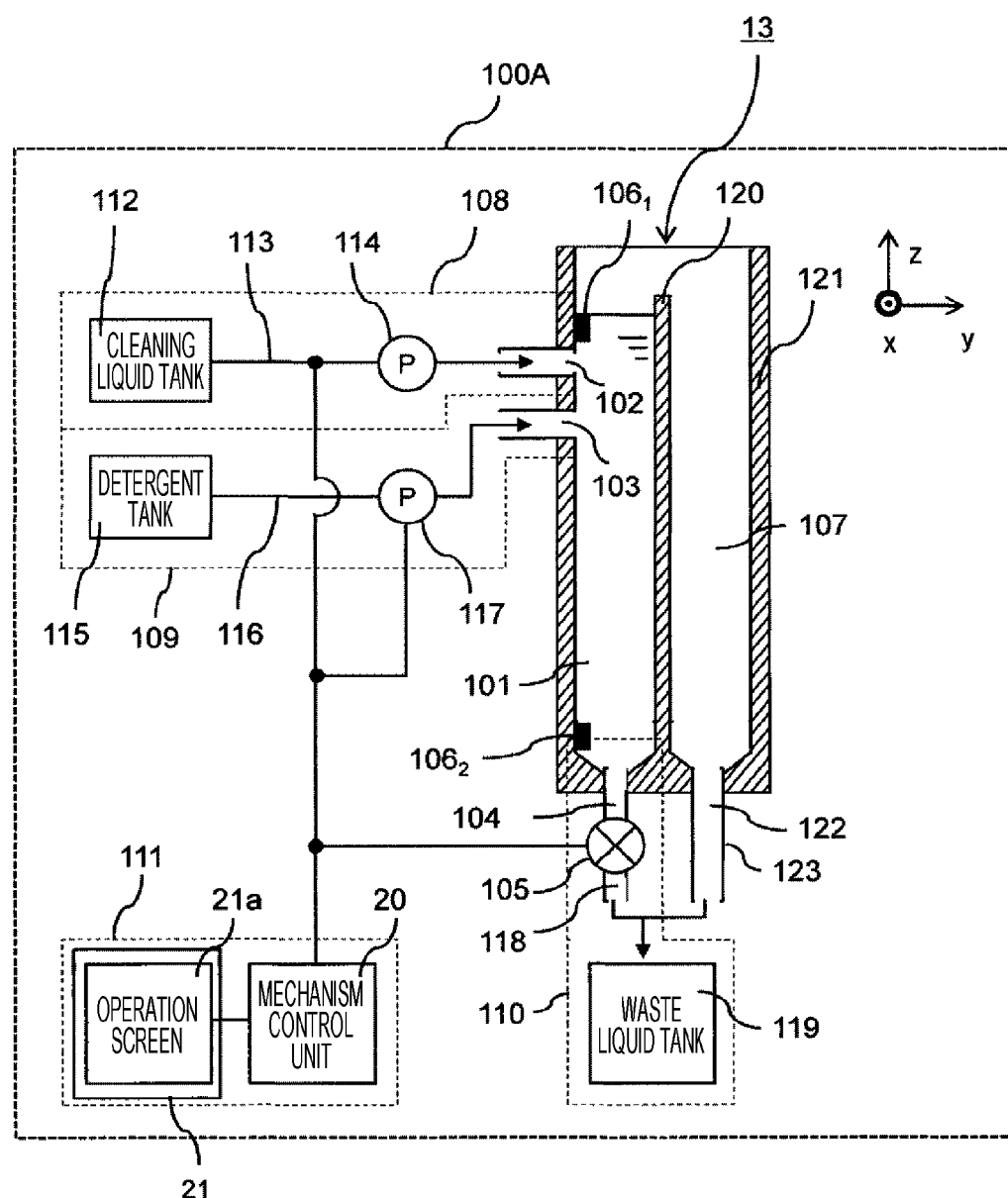
FIG. 2 is a configuration diagram of a detergent reservoir system for use in the automatic analyzer as the first embodiment of the present invention.

Next, a configuration of a detergent reservoir system 100A for use in the automatic analyzer 1000 as the first embodiment of the present invention will be described with reference to FIG. 2. FIG. 2 is a configuration diagram of the detergent reservoir system 100A for use in the automatic analyzer 1000 as the first embodiment of the present invention.

The detergent reservoir system 100A mainly includes the detergent reservoir unit 13, a cleaning liquid supply unit 108, a detergent supply unit 109, a waste liquid unit 110, and a control unit 111.

The detergent reservoir unit 13 includes a detergent reservoir 101, a cleaning liquid supply port 102, a detergent supply port 103, a waste liquid port 104, a solenoid valve 105, a liquid level sensor 106 ($106_1$ to $106_2$), and a waste liquid bath 107.

The dispensation probe of the sample dispensation mechanism 11 sucks the detergent reserved in the detergent reservoir 101 and discharges the sucked detergent into the waste liquid bath 107 or the cleaning bath 12. Thereafter, an inner wall and an outer wall of the dispensation probe are cleaned with purified water in the cleaning bath 12. Although the liquid level of the detergent reaches an upper part of the liquid level sensor $106_1$ in FIG. 2, the amount of the detergent reserved in the detergent reservoir 101 decreases each time the dispensation probe of the sample dispensation mechanism 11 sucks the detergent from the detergent reservoir 101.

The mechanism control unit 20 controls opening/closing of the solenoid valve 105. When the solenoid valve 105 is opened, detergent and cleaning liquid in the detergent reservoir 101 are drained. Conversely, when the solenoid valve 105 is closed, and the detergent is supplied, the detergent is reserved in the detergent reservoir 101. The liquid level sensor 106 detects a liquid level in the detergent reservoir 101.

Here, cleaning liquid (e.g., pure water and ion-exchange water) for use in cleaning of the detergent reservoir 101 is supplied from the cleaning liquid supply port 102, and detergent for use in cleaning of the dispensation probe is supplied from the detergent supply port 103.

The cleaning liquid supply port 102 is installed further on an upper side than the detergent supply port 103. By supplying the cleaning liquid from the cleaning liquid supply port 102, a crystal of the detergent attached to the detergent supply port 103 can be washed away.

To the detergent reservoir unit 13, the cleaning liquid supply unit 108, the detergent supply unit 109, the waste liquid unit 110, and the control unit 111 are connected.

The cleaning liquid supply unit 108 includes a cleaning liquid tank 112, a flow path 113 connecting the cleaning liquid tank 112 with the detergent reservoir 101, a pump 114 feeding the cleaning liquid from the cleaning liquid tank 112 to the detergent reservoir 101, and the cleaning liquid supply port 102.

The detergent supply unit 109 includes a detergent tank 115, a flow path 116 connecting the detergent tank 115 with the detergent reservoir 101, a pump 117 feeding the detergent from the detergent tank 115 to the detergent reservoir 101, and the detergent supply port 103.

The waste liquid unit 110 includes the waste liquid port 104, the solenoid valve 105, a flow path 118 connecting the waste liquid port 104 with a waste liquid tank 119, and the waste liquid tank 119.

The control unit 111 includes the mechanism control unit 20 and the display unit 21. The operator can input cleaning parameters specifying conditions for cleaning in the mechanism control unit 20 via the operation screen 21a displayed on the display unit 21. The mechanism control unit 227 controls operations of the respective peripheral mechanisms in accordance with the input cleaning parameters.

The waste liquid bath 107 is used when the dispensation probe of the sample dispensation mechanism 11 discharges the sucked detergent and when a liquid overflowing from a detergent reservoir port 120 is drained. Meanwhile, a configuration of the detergent reservoir port 120 will be described below with reference to FIG. 3.

The waste liquid bath 107 is adjacent to the detergent reservoir 101 and is surrounded by an external frame 121. The external frame 121 is provided with a waste liquid port 122. A liquid drained from the waste liquid port 122 passes through a flow path 123 and is disposed of into the waste liquid tank 119.

Figure 3:
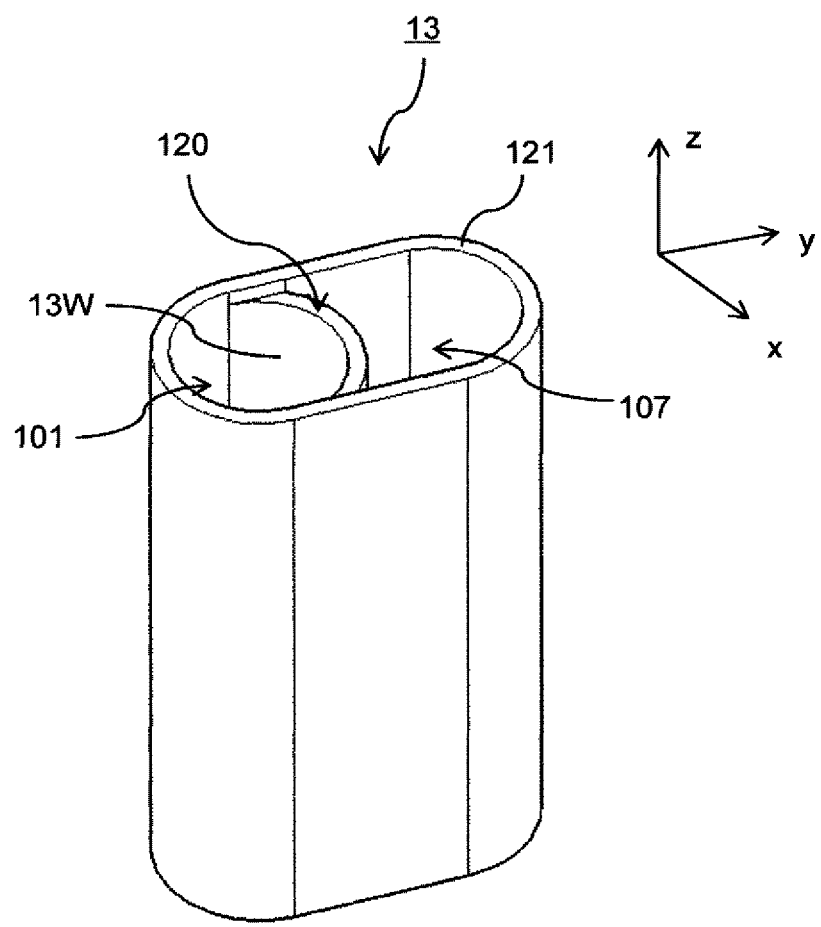
FIG. 3 is a perspective view of a detergent reservoir unit illustrated in FIG. 2.

Next, a configuration of the detergent reservoir unit for use in the automatic analyzer 1000 as the first embodiment of the present invention will be described with reference to FIG. 3. FIG. 3 is a perspective view of the detergent reservoir unit 13 illustrated in FIG. 2. Meanwhile, FIG. 3 illustrates only a main part for easy viewing.

An upper end surface of a partition wall 13W residing between the detergent reservoir 101 and the waste liquid bath 107 is lower than an upper end surface of the external frame 121. Accordingly, the detergent reservoir port 120 is formed.

Figure 4:
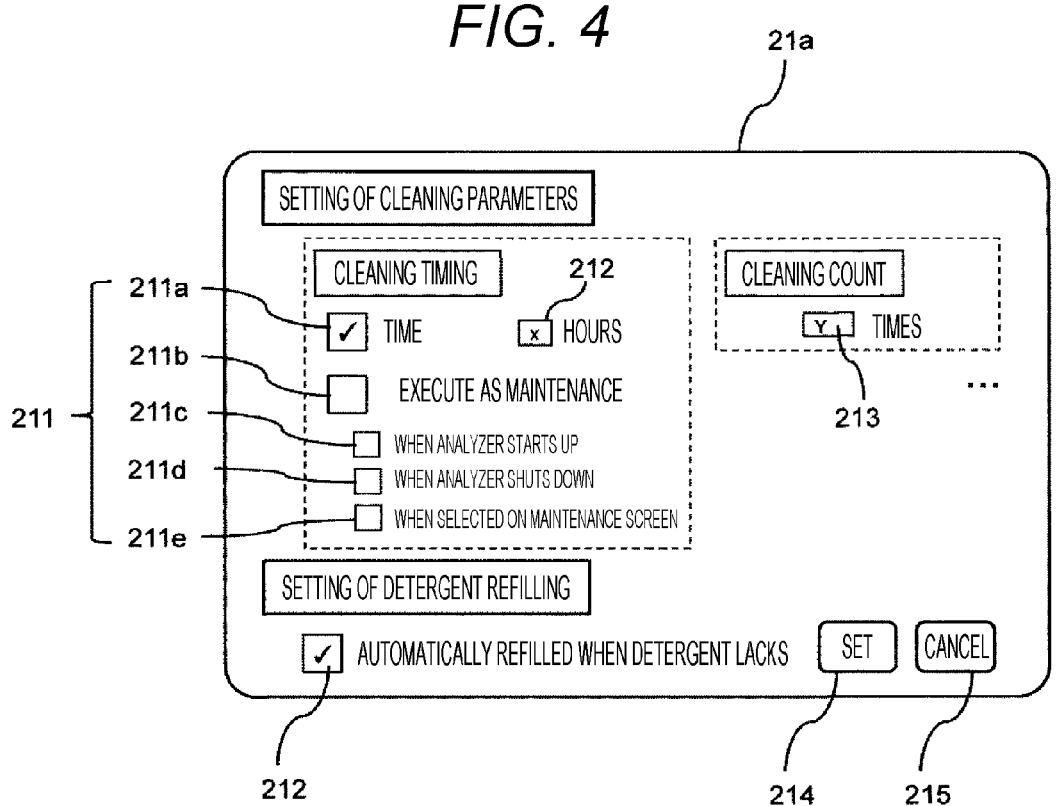
FIG. 4 illustrates an example of a configuration of an operation screen displayed on a display unit in the automatic analyzer as the first embodiment of the present invention.

Next, a configuration of the operation screen 21a displayed on the display unit 21 in the automatic analyzer 1000 as the first embodiment of the present invention will be described with reference to FIG. 4. FIG. 4 illustrates an example of a configuration of the operation screen 21a displayed on the display unit 21 in the automatic analyzer 1000 as the first embodiment of the present invention.

The operation screen 21a is a screen allowing the operator to register conditions for executing cleaning of the detergent reservoir 101. The operator registers cleaning parameters (cleaning timing, cleaning count, and the like of the detergent reservoir 101) in the analyzer via the operation screen 21a.

The operation screen 21a includes a check box 211 (211a to 211e) for setting cleaning timing (cleaning start trigger), a text box 212 for setting a cleaning interval, a text box 213 for setting the number of times of cleaning of the detergent reservoir 101 at cleaning timing, a setting button 214 for registering set conditions (cleaning parameters), and a cancel button 215 for cancelling the set conditions and hiding the operation screen 21a.

Here, the check boxes 211a to 211e for setting cleaning timing will be described specifically.

When the "Time" check box 211a is set to be on, cleaning of the detergent reservoir 101 is executed at intervals ("X" hours in the example in FIG. 4) set in the text box 212.

When the "Execute as maintenance" check box 211b is set to be on, cleaning of the detergent reservoir 101 is executed when the operator has started cleaning as part of analyzer maintenance (e.g., when a predetermined maintenance execution button has been pressed).

When the "When analyzer starts up" check box 211c is set to be on, cleaning of the detergent reservoir 101 is executed when the automatic analyzer 1000 is activated (e.g., when a power switch is turned on).

When the "When analyzer shuts down" check box 211d is set to be on, cleaning of the detergent reservoir 101 is executed when the automatic analyzer 1000 is exited (e.g., when a predetermined shutdown button has been pressed).

When the "When selected on maintenance screen" check box 211e is set to be on, cleaning of the detergent reservoir 101 is executed when a predetermined cleaning button giving instruction for execution of cleaning of the detergent reservoir 101 has been pressed on a maintenance screen for setting maintenance items.

In the example in FIG. 4, the dispensation probe of the sample dispensation mechanism 11 is cleaned every "X" hours. At this time, cleaning is performed "Y" times. Detailed description of a cleaning operation will be provided below with reference to FIG. 5.

Figure 5:
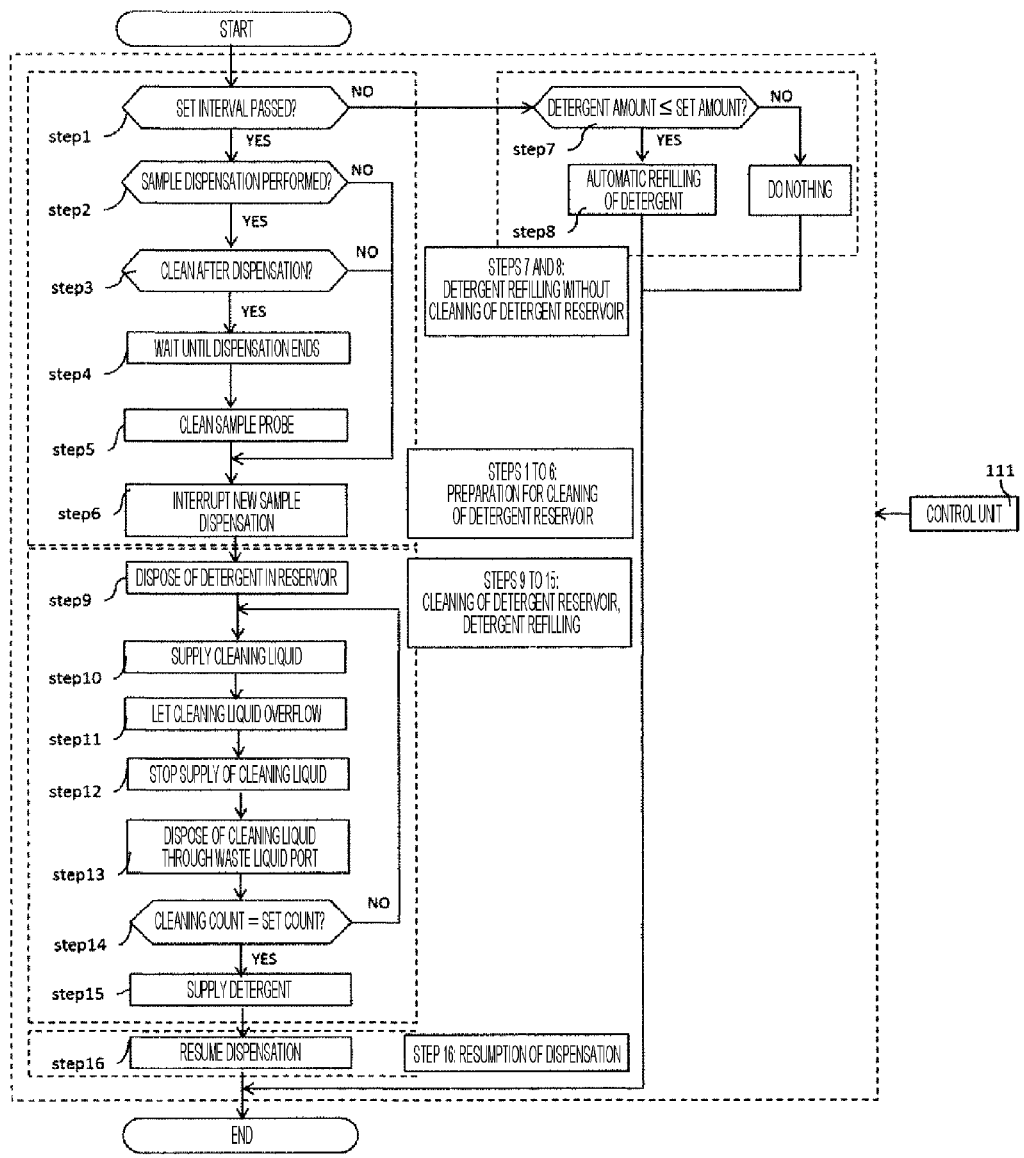
FIG. 5 is a flowchart illustrating an operation of the automatic analyzer as the first embodiment of the present invention.

Next, an operation of the automatic analyzer 1000 as the first embodiment of the present invention will be described with reference to FIG. 5. FIG. 5 is a flowchart illustrating an operation of the automatic analyzer 1000 as the first embodiment of the present invention. In the following description, the cleaning parameters shall be set as illustrated in FIG. 4 as an example.

First, in steps 1 to 6, preparation for cleaning of the detergent reservoir 101 is performed. Specifically, the mechanism control unit 20 determines whether or not "X" hours as a set interval have passed (step 1).

In a case in which the mechanism control unit 20 has determined that "X" hours set as a cleaning parameter have passed (step 1: YES), the mechanism control unit 20 determines whether or not a sample dispensation operation is being performed by the sample dispensation mechanism 11 (step 2).

In a case in which dispensation is being performed (step 2: YES), the mechanism control unit 20 determines whether or not the sample dispensation probe is to be cleaned with detergent after the current sample dispensation is finished (step 3). Specifically, the mechanism control unit 20 determines that the sample dispensation probe is to be cleaned with detergent in a case in which the sample that is currently being dispensed is a predetermined sample (e.g., whole blood).

In a case in which the mechanism control unit 20 has determined that cleaning is to be performed (step 3: YES), that is, in a case in which the detergent in the detergent reservoir 101 is to be used, the mechanism control unit 20 waits until the current sample dispensation is finished (step 4). When the current sample dispensation is finished, the mechanism control unit 20 cleans the sample dispensation probe with the detergent in the detergent reservoir 101 (step 5).

After cleaning the sample dispensation probe, the mechanism control unit 20 interrupts new sample dispensation (step 6). At this time, other mechanisms such as the reagent dispensation mechanism 7 and the photometer 4 are kept operated. Accordingly, reagent dispensation and photometric measurement are continued.

In a case in which sample dispensation is not being performed in step 2 (step 2: NO), or in a case in which the sample dispensation probe is not to be cleaned with the detergent after the current sample dispensation is finished in step 3 (step 3: NO), the processing directly proceeds to step 6.

On the other hand, in a case in which the mechanism control unit 20 has determined in step 1 that set "X" hours have not passed, the mechanism control unit 20 determines whether or not the amount of the detergent in the detergent reservoir 101 is a set amount or less (step 7). Specifically, the mechanism control unit 20 determines from the liquid level sensor $106_2$ installed at a lower part of the detergent reservoir 101 whether or not the amount of the detergent is the set amount or less.

In a case in which the amount of the detergent in the detergent reservoir 101 is the set amount or less (step 7: YES), the mechanism control unit 20 performs automatic refilling of the detergent (step 8). Specifically, the mechanism control unit 20 operates the pump 117 feeding the detergent from the detergent tank 115 to the detergent reservoir 101.

Subsequently, cleaning of the detergent reservoir 101 and refilling of the detergent are performed in steps 9 to 15. Specifically, the mechanism control unit 20 opens the solenoid valve 105 to dispose of the detergent in the detergent reservoir 101 (step 9). Subsequently, the mechanism control unit 20 closes the solenoid valve 105 and supplies the cleaning liquid from the cleaning liquid supply port 102 (step 10). Specifically, the mechanism control unit 20 operates the pump 114 feeding the cleaning liquid from the cleaning liquid tank 112 to the detergent reservoir 101.

The mechanism control unit 20 lets the supplied cleaning liquid overflow from the detergent reservoir port 120 to clean an inner wall of the detergent reservoir 101 (step 11). Specifically, the mechanism control unit 20 operates the pump 117 feeding the detergent from the detergent tank 115 to the detergent reservoir 101 for a predetermined period of time for the detergent reservoir 101. The predetermined period of time is a period of time longer than a period of time in which the pump 114 is operated to bring a state in which the detergent reservoir 101 is full of the detergent (maximum capacity) from a state in which the detergent reservoir 101 is empty.

The mechanism control unit 20 stops supply of the cleaning liquid after the lapse of a predetermined period of time (step 12) and opens the solenoid valve 105 to dispose of the cleaning liquid in the detergent reservoir 101 (step 13).

The mechanism control unit 20 determines whether or not the cleaning count has reached "Y" times, which is a set count set on the operation screen 21a (step 14). In a case in which the cleaning count has not reached the set count (step 14: NO), the mechanism control unit 20 performs processing in steps 10 to 13. In a case in which the cleaning count has reached the set count (step 14: YES), the mechanism control unit 20 supplies the detergent until the liquid level sensor $106_1$ detects the liquid level of the detergent (step 15).

Finally, the sample dispensation interrupted in step 6 is resumed (step 16), and the processing ends.

As described above, according to the present embodiment, cleaning of the detergent reservoir 101 can be performed automatically. This can reduce trouble of cleaning work of the detergent reservoir 101. Also, according to the present embodiment, the reagent dispensation and the photometric measurement are continued even during cleaning of the detergent reservoir 101. This can restrict a decrease in the analysis processing amount due to the detergent reservoir cleaning.

(First Modification Example)

Figure 6:
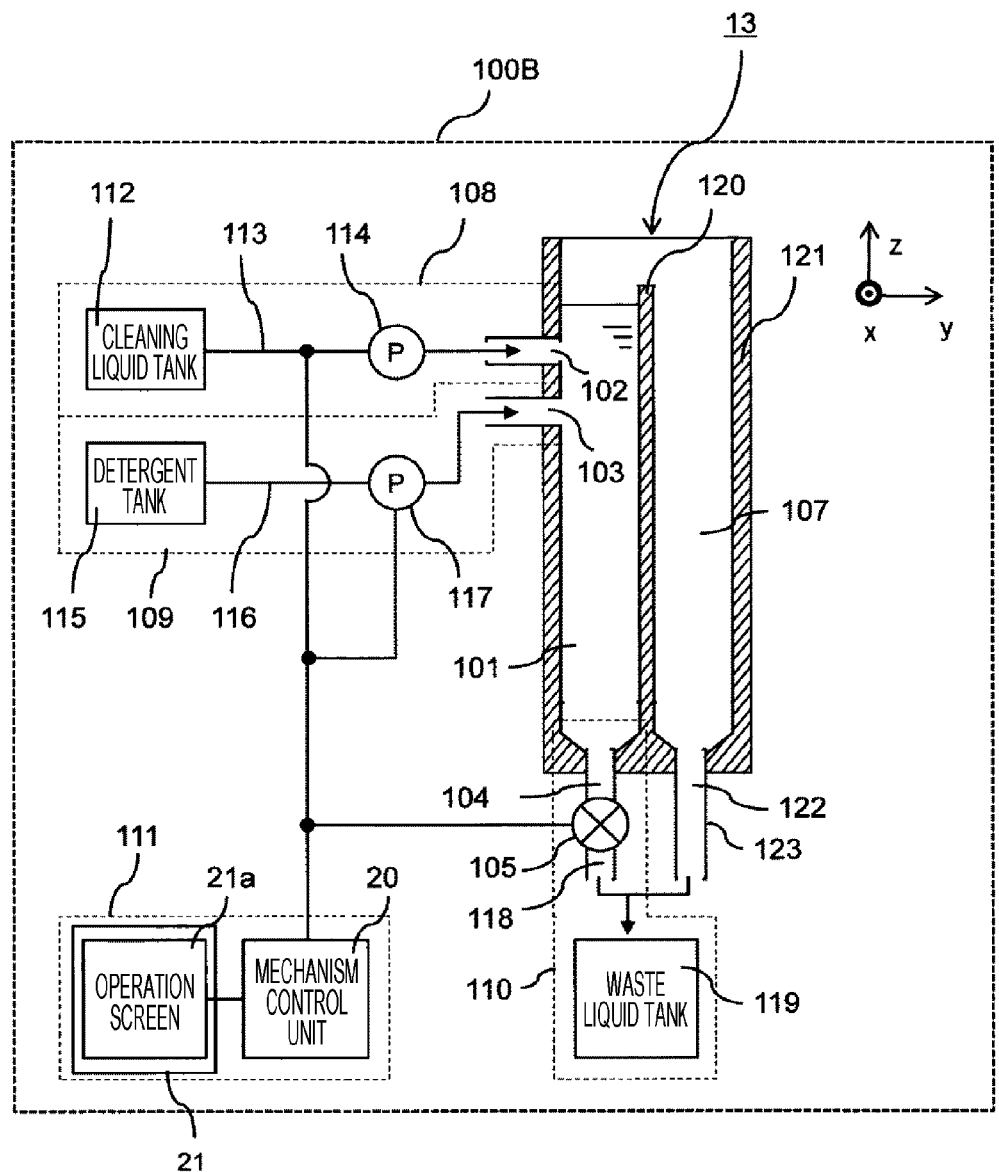
FIG. 6 is a configuration diagram of a detergent reservoir system for use in the automatic analyzer as a first modification example of the present invention.

Next, a configuration of a detergent reservoir system 100B for use in the automatic analyzer 1000 as a first modification example of the present invention will be described with reference to FIG. 6. FIG. 6 is a configuration diagram of the detergent reservoir system 100B for use in the automatic analyzer 1000 as the first modification example of the present invention. It is to be noted that similar or identical components to those in FIG. 2 are shown with the same reference numerals in FIG. 6.

Contrary to FIG. 2, the liquid level sensor 106 ($106_1$ to $106_2$) does not exist in FIG. 6. In the present modification example, the mechanism control unit 20 uses a liquid level sensor provided in the sample dispensation probe to measure liquid height of the detergent in the detergent reservoir 101 and determine the remaining amount of the detergent.

Meanwhile, the mechanism control unit 20 may determine the remaining amount by calculating the consumed amount of the detergent from the cleaning count of the sample dispensation probe and calculating the remaining amount from the amount of the detergent when the detergent is full and the calculated consumed amount of the detergent.

According to the first modification example, the detergent reservoir 101 needs to be provided with no liquid level sensor. Accordingly, manufacturing cost of the automatic analyzer can be reduced.

(Second Modification Example)

Figure 7:
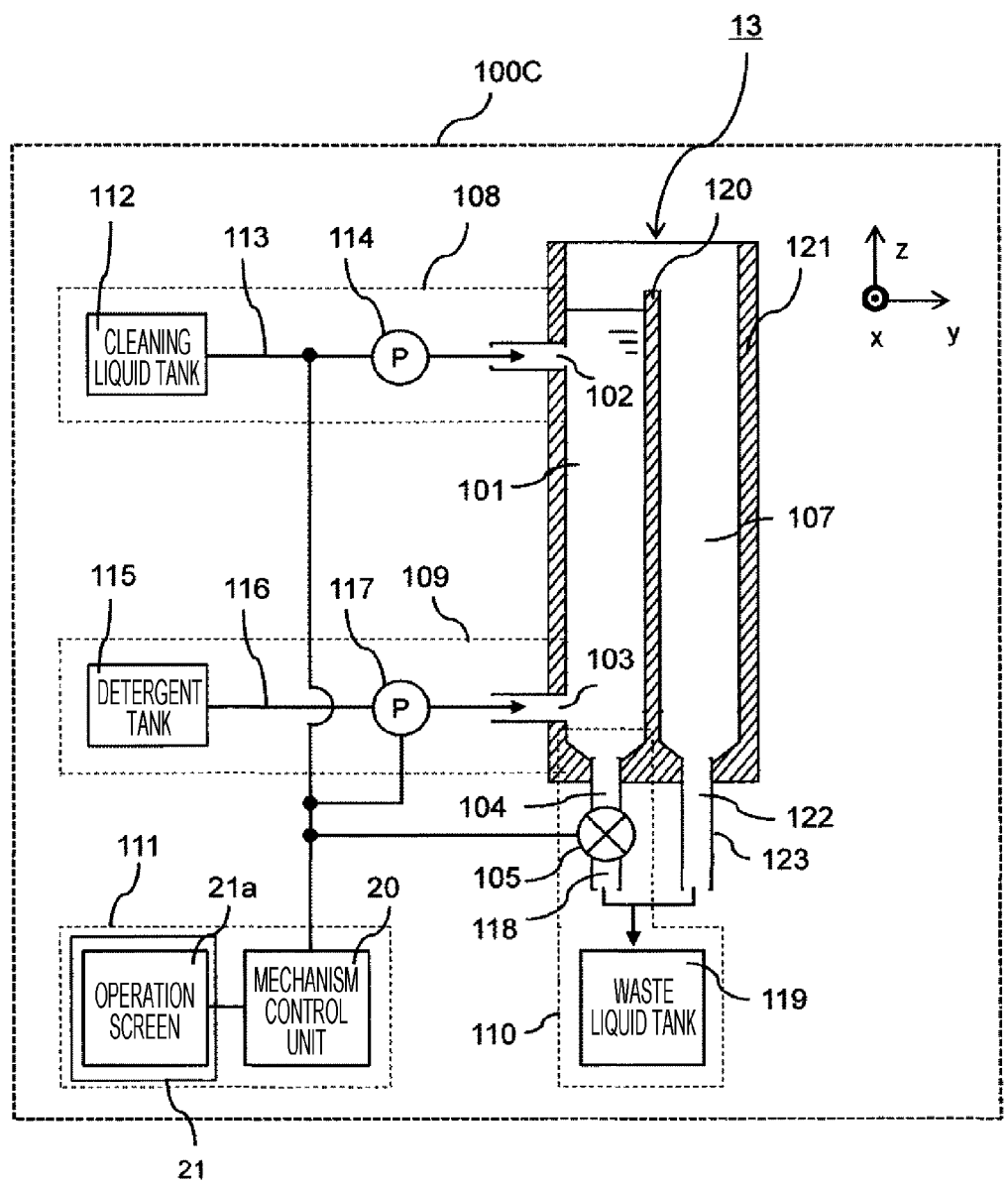
FIG. 7 is a configuration diagram of a detergent reservoir system for use in the automatic analyzer as a second modification example of the present invention.

Next, a configuration of a detergent reservoir system 100C for use in the automatic analyzer 1000 as a second modification example of the present invention will be described with reference to FIG. 7. FIG. 7 is a configuration diagram of the detergent reservoir system 100C for use in the automatic analyzer 1000 as the second modification example of the present invention. It is to be noted that similar or identical components to those in FIG. 6 are shown with the same reference numerals in FIG. 7.

In FIG. 7, the position of the detergent supply port 103 differs from that in FIG. 6. Specifically, in the present modification example, the detergent supply port 103 is arranged at an end part on a lower side (around a bottom part) of the detergent reservoir 101. Accordingly, since a period during which the detergent supply port 103 is soaking in the cleaning liquid in steps 11 and 12 is longer, the crystal is easily removed.

(Second Embodiment)

Figure 8:
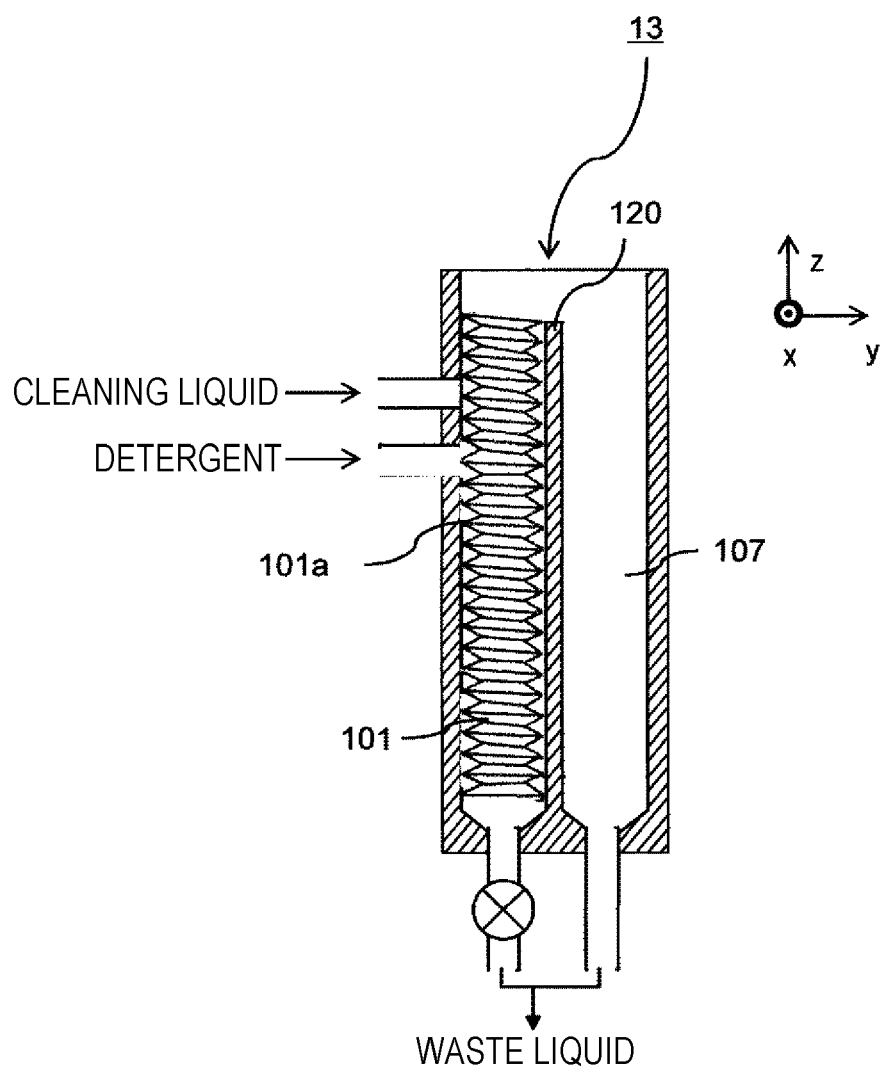
FIG. 8 is a configuration diagram (cross-sectional view) of a detergent reservoir for use in the automatic analyzer as a second embodiment of the present invention.

Next, a configuration of the detergent reservoir unit for use in the automatic analyzer 1000 as a second embodiment of the present invention will be described with reference to FIG. 8. FIG. 8 is a configuration diagram (cross-sectional view) of the detergent reservoir unit 13 for use in the automatic analyzer 1000 as the second embodiment of the present invention. It is to be noted that similar or identical components to those in FIG. 6 are shown with the same reference numerals in FIG. 8.

FIG. 8 differs from FIG. 6 in that the detergent reservoir unit 13 includes a spiral recess 101a on an inner circumferential surface of the detergent reservoir 101.

Here, in the first embodiment, the first modification example, and the second modification example, when the diameter of the detergent reservoir 101 is large, the cleaning liquid may not cover the entire inner wall of the detergent reservoir 101 to hinder uniform cleaning.

According to the present embodiment, since the cleaning liquid goes along the recess and flows over the entire inner wall of the detergent reservoir 101, the inner wall of the detergent reservoir 101 can be cleaned uniformly.

(Third Embodiment)

Figure 9:
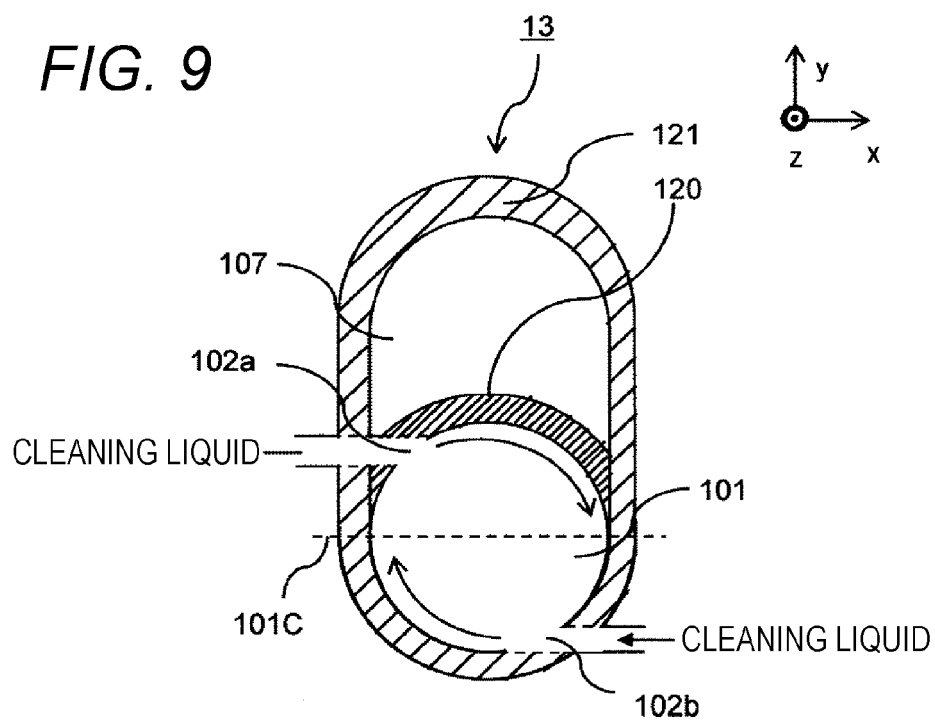
FIG. 9 is an upper view of the detergent reservoir unit for use in the automatic analyzer as a third embodiment of the present invention.

Next, a configuration of the detergent reservoir unit for use in the automatic analyzer 1000 as a third embodiment of the present invention will be described with reference to FIG. 9. FIG. 9 is an upper view of the detergent reservoir unit 13 for use in the automatic analyzer 1000 as the third embodiment of the present invention. It is to be noted that similar or identical components to those in FIG. 3 are shown with the same reference numerals in FIG. 9. FIG. 9 corresponds to an upper view of FIG. 3.

As illustrated in FIG. 9, the detergent reservoir unit 13 includes two cleaning liquid supply ports 102a and 102b.

The two cleaning liquid supply ports 102a and 102b are arranged to be displaced to the right and the left from a center line 101C perpendicular to an axis (an axis parallel to a z axis) of the detergent reservoir 101. In other words, the cleaning liquid supply ports 102a and 102b are arranged at point-symmetrical positions about a center of a circular cross-section (a cross-section vertical to the z axis) of the detergent reservoir 101.

In the present embodiment, at the time the cleaning liquid discharged from the cleaning liquid supply port 102a goes along the inner wall of the detergent reservoir and reaches the cleaning liquid supply port 102b, the cleaning liquid is discharged from the cleaning liquid supply port 102b. It is to be noted that the times of discharging the cleaning liquid from the cleaning liquid supply ports 102a and 102b are not limited to these, and that the cleaning liquid may be discharged from the cleaning liquid supply ports 102a and 102b at the same time.

According to the present embodiment, since the supplied cleaning liquid eddies in the detergent reservoir 101, the inner wall can be cleaned efficiently even when the diameter of the detergent reservoir 101 is large. This operation is controlled by the control unit 111.

(Fourth Embodiment)

Figure 10:
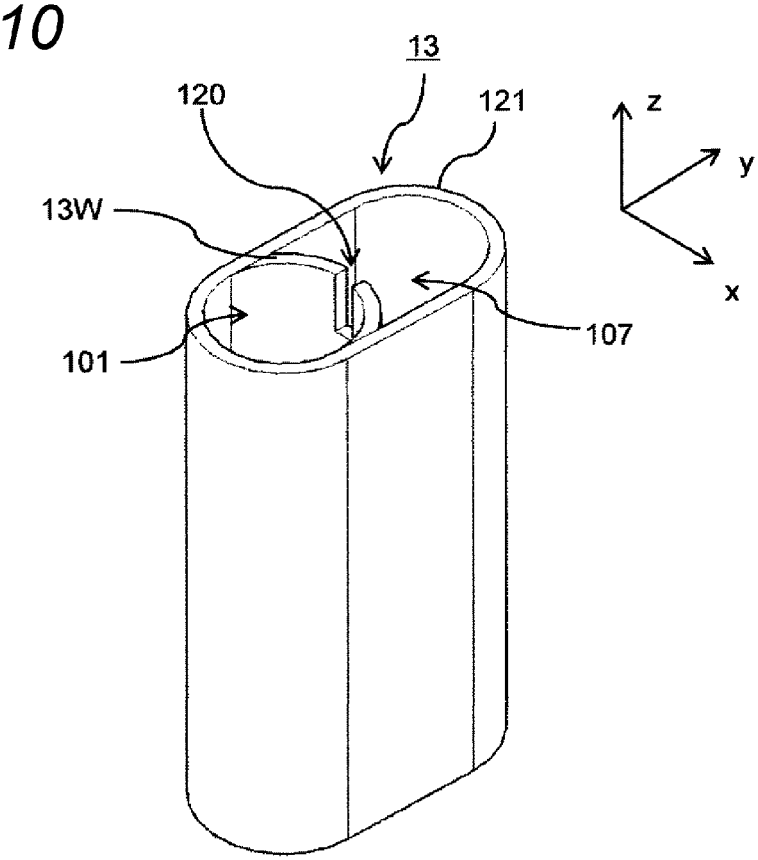
FIG. 10 is a configuration diagram (perspective view) of the detergent reservoir unit for use in the automatic analyzer as a fourth embodiment of the present invention.

Next, a configuration of the detergent reservoir unit for use in the automatic analyzer 1000 as a fourth embodiment of the present invention will be described with reference to FIG. 10. FIG. 10 is a configuration diagram (perspective view) of the detergent reservoir unit 13 for use in the automatic analyzer 1000 as the fourth embodiment of the present invention. It is to be noted that similar or identical components to those in FIG. 3 are shown with the same reference numerals in FIG. 10. Meanwhile, FIG. 10 illustrates only a main part for easy viewing.

FIG. 10 differs from FIG. 3 in that the recessed (slit-like) detergent reservoir port 120 is formed at the upper end of the partition wall 13W so that the cleaning liquid may overflow from the detergent reservoir 101 to the external frame 121.

Meanwhile, although the upper end surface of the partition wall 13W residing between the detergent reservoir 101 and the waste liquid bath 107 and the upper end surface of the external frame 121 are equal in terms of the position in the direction of the z axis in FIG. 10, the present invention is not limited to this. That is, the recessed (slit-like) detergent reservoir port 120 may be formed in the detergent reservoir unit 13 illustrated in FIGS. 3 and 9.

Figure 11:
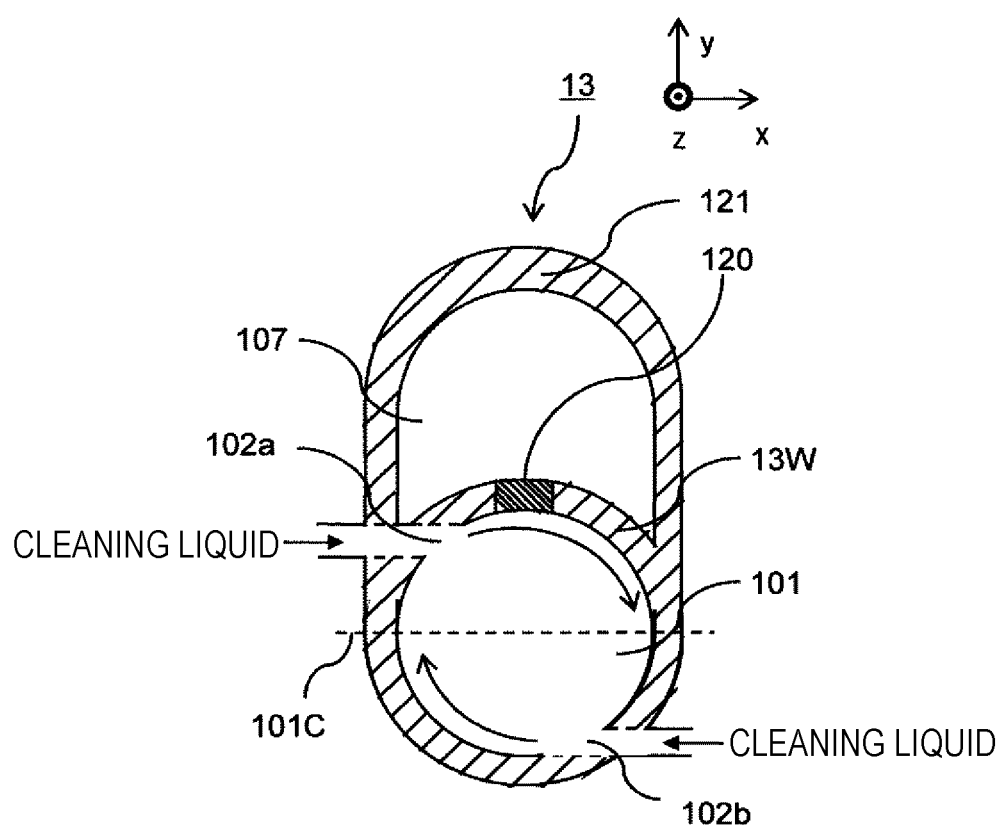
FIG. 11 is an upper view of the detergent reservoir unit illustrated in FIG. 10.

Next, the configuration of the detergent reservoir unit 13 for use in the automatic analyzer 1000 as the fourth embodiment of the present invention will be described with reference to FIG. 11. FIG. 11 is an upper view of the detergent reservoir unit 13 illustrated in FIG. 10.

According to the present embodiment, in a similar manner to that in the third embodiment, since the supplied cleaning liquid eddies in the detergent reservoir 101, the inner wall can be cleaned efficiently even when the diameter of the detergent reservoir 101 is large.

The present invention is not limited to the above embodiments and includes various modification examples. For example, each of the above embodiments has been described in detail to make the present invention understood easily, and the present invention is not necessarily limited to one including all of the aforementioned components. Part of the components in one embodiment can be replaced with part of the components in another embodiment or can be added to the components in another embodiment. Part of the components in each embodiment can be added to, deleted from, or replaced with the components in another embodiment.

Reference Signs List

| | |
|---|---|
| 1 | reaction disk |
| 2 | reaction cuvette |
| 3 | washing mechanism |
| 4 | photometer |
| 5 | stirring mechanism |
| 6 | cleaning bath |
| 7 | reagent dispensation mechanism |
| 8 | cleaning bath |
| 9 | reagent disk |
| 10 | reagent bottle |
| 11 | sample dispensation mechanism |
| 12 | cleaning bath |
| 13 | detergent reservoir unit |
| 14 | sample container |
| 15 | rack |
| 16 | sample transport mechanism |
| 17 | reagent pump |
| 18 | sample pump |
| 19 | washing pump |
| 20 | mechanism control unit |
| 21 | display unit |
| 100A, 100B, 100C | detergent reservoir system |
| 101 | detergent reservoir |
| 102 | cleaning liquid supply port |
| 103 | detergent supply port |
| 104 | waste liquid port |
| 105 | solenoid valve |
| 106 | liquid level sensor |

-continued

| Reference Signs List | |
|---|---|
| 107 | waste liquid bath |
| 108 | cleaning liquid supply unit |
| 109 | detergent supply unit |
| 110 | waste liquid unit |
| 111 | control unit |
| 112 | cleaning liquid tank |
| 113 | flow path |
| 114 | pump |
| 115 | detergent tank |
| 116 | flow path |
| 117 | pump |
| 118 | flow path |
| 119 | waste liquid tank |
| 120 | detergent reservoir port |
| 121 | external frame |
| 122 | waste liquid port |
| 123 | flow path |
| 1000 | automatic analyzer |

The invention claimed is:

1. An automatic analyzer comprising:
a sample dispensation mechanism dispensing a sample with use of a probe;
a cleaning bath in which cleaning of the probe is performed with purified water;
a detergent reservoir including at least one cleaning liquid supply port, a detergent supply port, and a waste liquid port, and the detergent reservoir reserves a detergent for cleaning of the probe, and in which, in a case in which the probe needs to be additionally cleaned based on a liquid property or a contained component of the sample, the probe is cleaned with the detergent;
a cleaning liquid tank storing a cleaning liquid for cleaning of the detergent reservoir;
a detergent tank storing the detergent;
a waste liquid tank;
a first pump installed on a flow path connecting the cleaning liquid tank with the cleaning liquid supply port;
a second pump installed on a flow path connecting the detergent tank with the detergent supply port;
a solenoid valve installed on a flow path connecting the waste liquid port with the waste liquid tank; and
a control unit configured to execute a first control in which, in a case in which a predetermined condition for execution of cleaning of the detergent reservoir is not satisfied, and in which a remaining amount of the detergent reserved in the detergent reservoir is a predetermined amount or less, the second pump is operated to increase the remaining amount of the detergent to the predetermined amount, and a second control in which, in a case in which the predetermined condition for execution of cleaning of the detergent reservoir is satisfied, the solenoid valve is opened to dispose of the detergent in the detergent reservoir, after the detergent in the detergent reservoir is disposed of, the solenoid valve is closed, and the first pump is operated to supply the cleaning liquid to the detergent reservoir.

2. The automatic analyzer according to claim 1, wherein the control unit is further configured to execute an analysis of the sample while the first control and the second control are being executed.

3. The automatic analyzer according to claim 2, wherein the control unit is further configured to, in the second control, operate the first pump to supply the cleaning liquid to overflow from the detergent reservoir and thereafter open the solenoid valve to dispose of the cleaning liquid in the detergent reservoir.

4. The automatic analyzer according to claim 3, wherein the control unit is further configured to:
interrupt dispensation of the sample and thereafter execute the second control,
open the solenoid valve to dispose of the cleaning liquid in the detergent reservoir and thereafter operate the second pump to increase the remaining amount of the detergent to the predetermined amount, and
resume the dispensation of the sample after the remaining amount of the detergent reaches the predetermined amount.

5. The automatic analyzer according to claim 1, wherein the cleaning liquid supply port is installed directly above the detergent supply port in the detergent reservoir.

6. The automatic analyzer according to claim 5, wherein the detergent supply port is installed at an end part on a lower side of the detergent reservoir.

7. The automatic analyzer according to claim 1, wherein the detergent reservoir includes a spiral recess on an inner circumferential surface thereof.

8. The automatic analyzer according to claim 1, wherein at least two cleaning liquid supply ports are arranged at point-symmetrical positions about a center of a cross-section vertical to an axis of the detergent reservoir.

9. The automatic analyzer according to claim 1, further comprising:
a waste liquid bath adjacent to the detergent reservoir and disposes of the cleaning liquid overflowing from the detergent reservoir.

10. The automatic analyzer according to claim 1, further comprising:
a display unit connected to the control unit,
wherein the control unit is further configured to display an operation screen for setting the predetermined condition for execution of cleaning of the detergent reservoir on the display unit.

11. An automatic analyzer comprising:
a sample dispensation mechanism dispensing a sample with use of a probe;
a cleaning bath in which cleaning of the probe is performed with purified water;
a detergent reservoir including: supply ports for cleaning liquid and detergent; and a waste liquid port, the detergent reservoir reserving detergent for cleaning of the probe, and in which, in a case in which the probe needs to be additionally cleaned based on the liquid property or the contained components of the sample, the probe is cleaned with detergent;
a cleaning liquid tank storing the cleaning liquid for cleaning the detergent reservoir;
a detergent tank storing the detergent;
a first pump installed on a flow path connecting the cleaning liquid tank with the detergent reservoir;
a second pump installed on a flow path connecting the detergent tank with the detergent reservoir; and
a control unit configured to execute a first control in which, in a case in which a predetermined condition for execution of cleaning of the detergent reservoir is not satisfied and in which a remaining amount of the detergent reserved in the detergent reservoir is a predetermined amount or less, the second pump is operated to increase the remaining amount of the detergent to the predetermined amount, and a second control in which, in a case in which the predetermined condition for execution of cleaning of the detergent reservoir is satisfied, the first pump is operated to supply the cleaning liquid to the detergent reservoir and make the cleaning liquid overflow from the detergent reservoir, wherein the supply ports for the cleaning liquid and the detergent are disposed lower than a liquid surface when the cleaning liquid overflows from the detergent reservoir.

12. The automatic analyzer according to claim 11, wherein the detergent reservoir is cleaned a preset number of times when a predetermined amount of time has passed, when the automatic analyzer starts up or when the automatic analyzer shuts down.

13. The automatic analyzer according to claim 11, further comprising:
  a waste liquid tank; and
  a solenoid valve installed on a flow path connecting the waste liquid port with the waste liquid tank.

14. The automatic analyzer according to claim 11, wherein the cleaning liquid is pure water or ion-exchange water.

15. An automatic analyzer comprising:
  a sample dispensation mechanism dispensing a sample with use of a probe;
  a cleaning bath in which cleaning of the probe is performed with purified water;
  a detergent reservoir including: supply ports for cleaning liquid and detergent; and a waste liquid port, the detergent reservoir reserving detergent for cleaning of the probe, and in which, in a case in which the probe needs to be additionally cleaned based on the liquid property or the contained components of the sample, the probe is cleaned with detergent;
  a cleaning liquid tank storing the cleaning liquid for cleaning the detergent reservoir;
  a detergent tank storing the detergent;
  a first pump installed on a flow path connecting the cleaning liquid tank with the detergent reservoir;
  a second pump installed on a flow path connecting the detergent tank with the detergent reservoir; and
  a control unit configured to execute a first control in which, in a case in which a predetermined condition for execution of cleaning of the detergent reservoir is not satisfied, and in which a remaining amount of the detergent reserved in the detergent reservoir is a predetermined amount or less, the second pump is operated to increase the remaining amount of the detergent to the predetermined amount, and a second control in which, in a case in which the predetermined condition for execution of cleaning of the detergent reservoir is satisfied, the first pump is operated to supply the cleaning liquid to the detergent reservoir and make the cleaning liquid overflow from the detergent reservoir,
  wherein the control unit is further configured to execute an analysis of the sample while the first control and the second control are being executed.

16. The automatic analyzer according to claim 11, wherein the supply ports for the cleaning liquid and the detergent include a supply port for the cleaning liquid disposed above a supply port for the detergent on the detergent reservoir.

17. The automatic analyzer according to claim 11, wherein the supply ports for the cleaning liquid and the detergent include a supply port for the detergent disposed on a lower side of the detergent reservoir closer to the waste liquid port than a supply port for the cleaning liquid.

18. The automatic analyzer according to claim 11, wherein the detergent reservoir includes a spiral recess on an inner circumferential surface thereof.

19. The automatic analyzer according to claim 11, wherein the supply ports for the cleaning liquid include two cleaning liquid supply ports arranged at point-symmetrical positions about a center of a cross-section vertical to an axis of the detergent reservoir.

* * * * *